(12) United States Patent
Pernodet et al.

(10) Patent No.: US 10,555,895 B2
(45) Date of Patent: Feb. 11, 2020

(54) **AQUEOUS EXTRACT OF *PRUNUS PERSICA* AND PROCESS FOR PREPARING THE SAME**

(71) Applicants: ISP Investments LLC, Wilmington, DE (US); ELC Management LLC, Melville, NY (US)

(72) Inventors: Nadine Pernodet, Huntington Station, NY (US); Dawn Layman, Ridge, NY (US); Jean-Marie Botto, Valbonne (FR); Elodie Oger, Vallauris (FR); Audrey Le Mestr, Antibes (FR); Isabelle Imbert, Cannes (FR); Nouha Domloge, Opio (FR)

(73) Assignees: ISP Investments LLC, Wilmington, DE (US); ELC Management LLC, Melville, NY (US)

( * ) Notice: Subject to any disclaimer, the term of this patent is extended or adjusted under 35 U.S.C. 154(b) by 0 days.

(21) Appl. No.: 16/330,020

(22) PCT Filed: Sep. 6, 2017

(86) PCT No.: PCT/US2017/050223
§ 371 (c)(1),
(2) Date: Mar. 1, 2019

(87) PCT Pub. No.: WO2018/048864
PCT Pub. Date: Mar. 15, 2018

(65) Prior Publication Data
US 2019/0201321 A1 Jul. 4, 2019

Related U.S. Application Data

(60) Provisional application No. 62/384,436, filed on Sep. 7, 2016.

(51) Int. Cl.
*A61K 36/00* (2006.01)
*A61K 8/9789* (2017.01)
*A61Q 19/08* (2006.01)
*A61Q 17/04* (2006.01)
*A61K 8/34* (2006.01)
*A61K 8/60* (2006.01)
*A61K 8/64* (2006.01)

(52) U.S. Cl.
CPC ............ *A61K 8/9789* (2017.08); *A61Q 17/04* (2013.01); *A61Q 19/08* (2013.01); *A61K 8/347* (2013.01); *A61K 8/60* (2013.01); *A61K 8/64* (2013.01); *A61K 2800/70* (2013.01); *A61K 2800/805* (2013.01)

(58) Field of Classification Search
CPC ..................................................... A61K 36/00
USPC ......................................................... 424/725
See application file for complete search history.

(56) References Cited

FOREIGN PATENT DOCUMENTS

| JP | 2001302439 A | 10/2001 |
| JP | 2008247783 A | 10/2008 |
| WO | WO2013050697 A2 | 4/2013 |

OTHER PUBLICATIONS

Database GNPD [Online] Mintel ; May 31, 2015 (May 31, 2015), Amorepacific: "Essence Gel SPF 40 PA++", XP002774803, Database accession No. 3161623 the whole document.
International Search Report of the application No. PCT/US2017/050223 Publication No. WO 2018/048864 A1 Publication Date Mar. 15, 2018.

*Primary Examiner* — Michael V Meller
(74) *Attorney, Agent, or Firm* — William J. Davis

(57) ABSTRACT

The present invention provides a process for obtaining an extract from peach flower extract (*Primus persica L.*) for skin cosmetic use, a peach flower extract obtainable by the process and a cosmetic composition comprising the said extract. The invention further provides a method for modulating the SIRT2 expression, a method of treatment designed to reduce and/or correct the signs of aging and photo-aging of the skin and keratinous appendages, and to protect the skin against aggressions due to ultraviolet radiation.

1 Claim, 5 Drawing Sheets

AQUEOUS EXTRACT OF *PRUNUS PERSICA* AND PROCESS FOR PREPARING THE SAME

TECHNICAL FIELD

The present invention is in the field of cosmetics and more specifically in the field of skin care. The invention relates to a process for preparing a peach flower (*Prunus Persica*) extract by aqueous extraction, a peach flower extract obtainable by the process and a cosmetic composition comprising the peach flower extract.

The invention also relates to a method for modulating the SIRT2 expression, to a cosmetic method of treatment designed to reduce and/or correct the signs of aging and photo-aging of the skin and keratinous appendages, and to protect the skin against aggressions due to ultraviolet radiation.

The Peach flower extract can be used alone or in combination with other active agents.

BACKGROUND

The skin is a vital organ composed of several layers (dermis, proliferative layers and stratum corneum), which covers the entire surface of the body and ensures protective, sensitive, immune, metabolic or thermoregulatory functions. The skin, like the other organs, is subject to aging.

For example, the appearance of the skin is modified by various types of internal (disease and hormonal changes such as pregnancy) or external aggressions (environmental factors, such as pollution, sunlight, pathogens, etc.). Then wrinkles and fine lines, hyperpigmentation or hypopigmentation blemishes, dryness or even dehydration of the skin, thinning of the epidermis, elastosis, imperfections, age spots, etc., may appear. All of these changes affect not only the skin, but also the keratinous appendages such as the nails and hair.

It is known that free radicals, chemically unstable and very reactive species generated by the intracellular metabolism or external aggressions, play a key role in the aging process and more particularly in the formation of oxidized, damaged proteins (Harman et al. "Aging: a theory based on free radical and radiation chemistry" J. Gerontol., 11, 298-300). These external aggressions can include: ultraviolet radiation, toxins, atmospheric pollutants, alimentary oxidants. Ultraviolet radiations skin exposure induces extensive generation of reactive oxygen species (ROS). These can react with DNA, proteins, fatty acids and saccharides causing oxidative damage.

In the skin, premature aging is observed, occurring in the areas exposed to ultraviolet radiation, characterized by phenomena of alteration to the macromolecules (lipidic peroxidation, carbonylation of proteins), affecting in particular elastin, collagen or fibronectin.

One of the important consequences of the accumulation of oxidative damage is a reduction in the capacity of the cell to produce ATP (Porteous et al., Eur J Biochem 1998, 257(1): 192-201). Thus, the phenomenon of cellular aging is in relation to the oxidative damage which the cell undergoes, but also to the process of energy production necessary for the cell to survive.

The human sirtuin family comprises 7 proteins, very conserved throughout evolution, named SIRT1 to SIRT7. "SIRT2 protein" is predominantly located in the cytoplasm and plays roles in oxidative stress response, inflammation, mitotic progression, microtubule dynamics, cell migration, longevity. In cytoplasm, SIRT2 co-localizes with and deacetylates microtubules. During mitosis, it is translocated to the nucleus where it deacetylates histone and regulates chromosomal condensation (Serrano L. et al., "The tumor suppressor SirT2 regulates cell cycle progression and genome stability by modulating the mitotic deposition of H4K20 methylation", Genes & Dev. 2013. 27: 639-653). Thereby, SIRT2 plays mitotic checkpoint role: it regulates the mitotic progression and the mitotic exit (Bosch-Presegué L. and Vaquero A., "Sirtuins in stress response: guardians of the genome", Oncogene (2014) 33, 3764-3775). Moreover, the stability of spindle assembly checkpoint protein BubR1 is under control of SIRT2 and a decline in BubR1 over time has been linked to mammalian aging (North B. J. et al., "SIRT2 induces the checkpoint kinase BubR1 to increase lifespan", The EMBO Journal, 2014, 33, Issue 13, 1438-1453). SIRT2 can therefore be associated with increased cell longevity through BubR1 pathway preservation.

Deacetylation of Lys668 of BubR1 by SIRT2 inhibits the ubiquitination of BubR1 and its designation to the proteasome. Germline mutation that reduce BubR1 abundance cause aneuploidy.

From the state of the art, numerous cosmetics are known which in some way contain plant-based raw materials in the form of oils or extracts. In most cases, the known advantageous effects of individual plants are used to achieve a corresponding overall effect.

The aim of the invention was to develop a novel plant extract exhibiting activation of the SIRT2 expression. Patent EP1868632 disclosed synthetic peptides able to activate endogenous synthesis of sirtuin (SIRT1) protein and have been identified by inventors to be able to activate SIRT 2. Based on this knowledge, the inventors searched for botanicals comprising sequence homology to those identified activating SIRT2 peptides. Sequence similarity searches to identify homologous sequences were performed using comprehensive protein sequence data bases like BLAST following standard procedures (William Pearson, "An Introduction to Sequence Similarity ("Homology") searching", Curr Protoc Bioinformatics. June 2013). This search allowed the inventors to select *Prunus persica* as a good candidate.

The peach flower extract according to the invention has shown an increased expression of sirtuin SIRT2 proteins in the skin.

The species name *Prunus persica* refers to its widespread cultivation in Persia, whence it was transplanted to Europe. It belongs to the genus *Prunus* which includes the cherry and plum, in the family Rosaceae. Genetic studies suggest peaches originated in China, where they have been cultivated since the early days of Chinese culture circa 2000 BC.

*Prunus persica* has long been used in Chinese medicine for treating skin disorder. In Korea, flowers have always been a favorite source of inspiration for women and men of letters. In addition to this quality of muse, flowers have been used in the life of every day, for food decoration or infusions.

The peach blossom is the symbol of Korea Feminine Beauty. The infusion with peach blossoms was once very popular among women of high social rank who knew its beneficial properties for the skin tone. Peach blossom, popularly consumed as tea, is believed to promote healthy, young-looking skin. The literature reporting pharmacological studies related to peach blossom is very limited.

Peach flower is known to be very rich in polyphenolic compounds, such as phenolic acids, and flavonoids. These molecules can act as scavengers of superoxide anions, singlet oxygen, hydroxyl radicals, and lipid peroxyl radicals.

Many flavonoids such as quercetin, luteolin and catechins are better antioxidants than the nutrients vitamin C and beta-carotene (Svobodova et al., "Natural phenolics in the prevention of UV-induced skin damage. A Review" Biomed. Papers 147(2), 137-145 (2003)). The controlled hydrolysis enables these compounds to be released. The peach leaves are used as an anthelmintic, and sedative in traditional medicine (Nadkarni, 1976). Cevallos-Casals et al. reported that peach fruits rich in phenolic and anthocyanin have good antioxidant and antimicrobial activities (Cevallos-Casals et al., "Selecting new peach and plum genotypes rich in phenolic compounds and enhanced functional properties", Food Chemistry 96 (2006) 273-280). The pink-colored peach blossom flowers, popularly consumed as tea, are purgative and are believed to promote healthy, young-looking skin. The peach blossom is the symbol of Korea Feminine Beauty. The infusion with peach blossoms was once very popular among women of high social rank who knew its beneficial properties for the skin tone.

Some flavonoids have been identified in peach flower such as the kaempferol glycoside derivatives multiflora B, trifolin, afzelin, and astragalin. In addition, a skin protection effect was demonstrated for multiflora B (Young ha Kim et al., "The extract of the flowers of *Prunus persica*, a new cosmetic ingredient, protects against solar ultraviolet-induced skin damage in vivo", j. Cosmet. Sci., 53, 27-34 (January/February 2002)).

Peach flowers which are pink in color have been used to obtain the extract. Flowers are rich in polyphenolic compounds and also in flavonoids in particular pink flower are also rich in particular flavonoids, the anthocyanins that give the pink color to the flower in comparison to white flower.

Anthocyanins have been demonstrated to have a broad spectrum of biological functions and may act as good antioxidant like other members of flavonoids family.

Antioxidants play an important role as health protecting factor. Primary sources of naturally occurring antioxidants are whole grains, fruits, flower and vegetables. Plant antioxidants are vitamin C, vitamin E, carotenes, phenolic acid, flavonoids. They have been recognized as having the potential to reduce disease risk, anti-aging effect. The antioxidant effect of pink peach blossom extract has been investigated according to the method of 2,2-Diphenyl-1-picrylhydrazyl (DPPH).

The use of peach extract in a cosmetic composition is known in prior art. Most extract are total extracts or water-alcohol extracts. For example, the Japanese patent application, JP-A-2001302439 has disclosed a cosmetic having inhibitory action on elastases and collagenases for prevention of skin aging by including an extract from white *Prunus Persia* Batsh obtained by high temperature extracting process. Korean patent, KR-526637 has disclosed an anti-ultraviolet and cosmetic composition for skin aging protection including ferulic acid and peach blossom extract in which the stability of skin including the extract from peach Blossom of 0.1-20.0 weight % and ferulic acid of 0.1-20.0 weight % in the active ingredient is improved. Japanese patent application, JP-A-2016053008 has disclosed a manufacturing method of the peach extract which has the active oxygen eliminating ability carrying out partition extraction of the obtained extract with hexane/water further, and contains sphingoglycolipid (ceramide component). Korean patent, KR-1429117 has disclosed a composition for skin whitening containing peach blossom extract obtained by a step of removing the flower (fuse) from the peach blossom and using only the calyx, drying the sample, pulverizing the sample, subjecting to the homogenizer. With the step of extracting in the solvent selected in the group consisting of water, lower alcohol of the C3-6 and lower organic acid of the C3-6. The obtained extract is freeze-dried after it filtering with filter paper. Unlike the prior art, the present application provides an effective process for extraction of peach flower extract with high polyphenol content and free of ceramide.

In spite of the various anti-aging cosmetic products on the market for the treatment of skin, there remains a need for effective topically applied cosmetic compositions that provide anti-aging or rejuvenating benefits to the skin, hair and/or nails using natural ingredients as active agent. Unnatural, chemically-synthesized products may be perceived as being environmentally or personally unsafe. In contrast, natural products are perceived as pure, mild, and superior to chemically synthesized products. Numerous natural based products extracted from plants or herbs are known to contain antioxidant/free-radical scavenging agents that can neutralize the effects of free-radical damage. Additionally, they can contain agents that stimulate the synthesis and restoration of damaged connective tissue structures in the dermis and barrier function in the epidermis.

There remains a need for cosmetic compositions which address the signs of aging, in particular the appearance of wrinkles, lines, and sagging. It is therefore an object of the present invention to provide new compositions and methods for treating, ameliorating, and/or preventing signs of aged or aging skin. It is a further object of the invention to improve the overall appearance of aging or aged skin.

The foregoing introduction is presented solely to provide a better understanding of the nature of the problems confronting the art and should not be construed in any way as an admission as to prior art nor should the citation of any reference herein be construed as an admission that such reference constitutes "prior art" to the instant application.

SUMMARY

The main aspect of the present invention provides a process for obtaining an extract containing flowers of plants of the genus *Prunus persica L.*, comprising the following steps:
(i) adding water to peach flower to make a mixture,
(ii) agitating the said mixture by maintaining temperature from room temperature (RT) to above 70° C.
(iii) filtering the mixture to remove the solid flower part to obtain the extract.

In another aspect, the present invention provides a cosmetic composition comprising peach flower extract obtained by aqueous extraction, wherein the peach flower extract comprises compounds having a molecular weight of less than 10 kDa in a physiologically acceptable medium.

In yet another aspect, the present invention provides a method for reducing and/or correcting the signs of aging and photo-aging of the skin and keratinous appendages, comprising topically applying to the skin, the mucous membranes and/or superficial skin appendages a cosmetic composition comprising peach flower extract obtained by aqueous extraction, wherein the peach flower extract comprises compounds having a molecular weight of less than 10 kDa in a physiologically acceptable medium.

The yet another aspect, the present invention provides method for modulating the SIRT2 expression, comprising topically applying to the skin, the mucous membranes and/or superficial skin appendages a cosmetic composition comprising peach flower extract obtained by aqueous extraction, wherein the peach flower extract comprises compounds having a molecular weight of less than 10 kDa in a physiologically acceptable medium.

BRIEF DESCRIPTION OF THE DRAWINGS

Further embodiments of the present invention can be understood with the appended figures.

DETAILED DESCRIPTION

Figure 1:
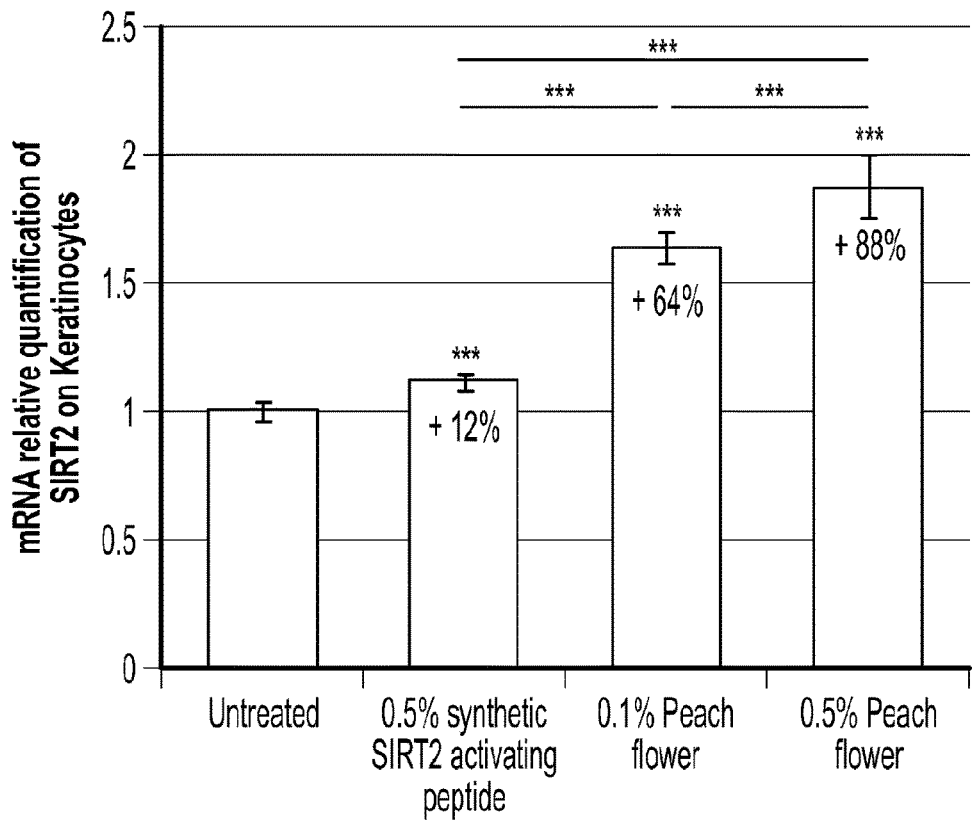
FIG. 1 is illustration of quantification of SIRT2 mRNA study on keratinocytes

Detailed embodiments of the present invention are disclosed herein; however, it is to be understood that the disclosed embodiments are merely illustrative of the invention that may be embodied in various forms. Therefore, specific structural and functional details disclosed herein are not to be interpreted as limiting, but merely as a representative basis for teaching one skilled in the art to variously employ the present invention.

Whenever a term is identified by reference to a range, the range will be understood to explicitly disclose every element thereof. As a non-limiting example, a range of 1-10% will be understood to include 1%, 2%, 3%, 4%, 5%, 6%, 7%, 8%, 9%, and 10%, and all values between 1 and 10%.

Where two or more substituents are referred to as being "selected from" a group of enumerated alternatives, it is meant that each substituent can be any element of that group, independent of the identity of the other substituents.

As used herein, "% refers % by weight, that is the weight percent of a component in relation to the total weight of the composition (i.e., including any carriers, vehicles, solvents, fillers, or other components added before application to the skin) unless otherwise provided.

All terms used herein are intended to have their ordinary meaning unless otherwise provided. For the purposes of describing and claiming the present invention, the following terms are defined:

"Extract" is understood to be any substance or isolated preparation extracted from a natural source, regardless of extraction method or ingredients. The term is used in a broad sense including, for example, ingredients soluble in water or an organic solvent extracted from a natural substance using the solvent, or specific ingredients of a natural substance.

"Aqueous extract" is understood to be a mixture of compounds obtained by extraction with water.

The term "peptide" indicates a sequence of two or several amino acids linked together by peptide bonds or by modified peptide bonds; and a polypeptide indicates a peptide of larger size. The term "peptide" refers to a natural or synthetic peptide of the invention as described above or at least any natural or synthetic peptide whose sequence is totally or partly constituted by the sequence previously described.

It is understood by "physiologically acceptable" that the active agent according to the invention, or a composition containing said agent, is suitable for coming into contact with the skin or a mucus membrane without provoking a toxicity or intolerance reaction.

"Cutaneous signs of aging and photo-aging" refers to all changes in the external appearance of the skin and skin appendages due to aging, such as, for example, thinning of the skin, sagging, loss of hydration and atonia, deep wrinkles and fine lines, loss of firmness and tone, dermal atrophy or any other internal degradation of the skin resulting from exposure to ultraviolet radiation, liver spots and age spots. Liver spots also known as "Solar lentigo", "Lentigo senilis", "Old age spot", "Senile freckle", are blemishes on the skin associated with aging and photo-aging due to exposure to ultraviolet radiation from the sun. They range in color from light brown to red or black and are located in areas most often exposed to the sun, particularly the hands, face, shoulders, arms and forehead, and the scalp if bald.

"Anti-Aging Benefit" Anti-aging benefits include, but are not limited to, one or more of: (a) treatment, reduction, and/or prevention of fine lines or wrinkles, (b) reduction of skin pore size, (c) improvement in skin thickness, plumpness, and/or tautness; (d) improvement in skin suppleness and/or softness; (e) improvement in skin tone, radiance, and/or clarity; (f) improvement in procollagen and/or collagen production; (g) improvement in skin texture and/or promotion of retexturization; (h) improvement in skin barrier repair and/or function; (i) treatment and/or prevention of skin sagging or atrophy; (j) improvement in appearance of skin contours; (k) restoration of skin luster and/or brightness; (l) replenishment of essential nutrients and/or constituents in the skin; (m) improvement of skin appearance decreased by menopause; (n) improvement in skin moisturization and/or hydration; and (o) improvement of skin elasticity and/or resiliency.

The species name "*Prunus persica*" in the present invention refers to its widespread cultivation in Persia, whence it was transplanted to Europe. It belongs to the genus *Prunus* which includes the cherry and plum, in the family Rosaceae. Genetic studies suggest peaches originated in China, where they have been cultivated since the early days of Chinese culture circa 2000 BC. *Prunus persica* has long been used in Chinese medicine for treating skin disorder (Young ha Kim et al., "The extract of the flowers of *Prunus persica*, a new cosmetic ingredient, protects against solar ultraviolet-induced skin damage in vivo", j. Cosmet. Sci., 53, 27-34, January-February 2002).

As used herein, "skin" refers to all of the covering tissue constituting the skin, the mucous membranes and the skin appendages, including hair, eyelashes and eyebrows.

"Topical application" is understood to be the application or spreading of a composition containing said peach flower extract, on the surface of the skin or a mucus membrane.

What is described herein is a process for obtaining an extract from dried peach flower, cosmetic composition comprising the extract, method of reducing and/or correcting the signs of aging and photo-aging of the skin and keratinous appendages by topically applying the composition comprising peach flower extract to the skin and a method for modulating the SIRT2 expression.

Antioxidants play an important role as health protecting factors. Scientific evidence suggests that antioxidants reduce the risk for chronic diseases including cancer and heart disease. Primary sources of naturally occurring antioxidants are whole grains, fruits, flower and vegetables. Plant antioxidants are vitamin C, vitamin E, carotenes, phenolic acid, flavonoids.

The peach flower extract according to the invention has shown an increased expression of sirtuin SIRT2 proteins in the skin. "SIRT proteins" are NAD+ dependent deacetylase and belong to the Sir2 sirtuin family. The deacetylase or mono-ADP-ribosyltransferase activity of sirtuins enables them to modulate the acetylation level of some histones. Thus, they often exert their functions by affecting chromatin, inducing gene silencing, DNA damage signaling, DNA repair and cell cycle regulation. Indeed, sirtuins are crucial factors in response to metabolic, oxidative or genotoxic stresses.

The peach flower extract according to the invention is known to be rich in polyphenolic compounds, such as phenolic acids, and flavonoids. All these water-soluble molecules known for their antioxidant activity contribute to provide the antioxidant potent of the peach flower extract according to the invention. Flavonoid content in the extract was estimated by Aluminum chloride colorimetric method. The principle involved in aluminium chloride (AlCl) colorimetric method is that AlCl3 forms acid stable complexes with the C-4 keto groups and either the C-3 or C-5 hydroxyl group of flavones and flavonols of the extract. The absorbance of the sample is read on the spectrophotometer at 410 nm. The flavonoid content is determined as rutin equivalent using a rutin standard curve. Total flavonoids content measured is 200 mg/kg of the extract.

These molecules can act as scavengers of superoxide anions, singlet oxygen, hydroxyl radicals, and lipid peroxyl radicals. Many flavonoids such as quercetin, luteolin and catechins are better antioxidants than the nutrients vitamin C, vitamin E and beta-carotene (Svobodova et al., "NATURAL PHENOLICS IN THE PREVENTION OF UV-INDUCED SKIN DAMAGE. A REVIEW" Biomed. Papers 147(2), 137-145 (2003)). Particularly pink flower are found to be rich in particular flavonoids, the anthocyanins that give the pink color to the flower in comparison to white flower.

In a preferred embodiment, pink flower has been used to obtain the extract according to the invention.

Polyphenolic compounds are recognized to be powerful antioxidant molecules. "Polyphenolic compounds" are compounds found abundantly in natural plant food sources that have antioxidant properties. They refer to all the classes of polyphenols, they mean compounds comprising at least one diphenol aromatic ring, phenol group may be optionally etherified or esterified. They can also be called simply "polyphenol". Polyphenols play an important role in maintaining your health and wellness. Antioxidants as a group help protect the cells in your body from free radical damage, thereby controlling the rate at which you age. Antioxidants can be divided into three major groups: Carotenoids, Allyl sulfides, found in garlic and onions, Polyphenols (also known as phenolics).

Polyphenols can be further broken down into four categories: phenolic acids, flavonoids, lignans, and stilbenes, with additional subgroupings based on the number of phenol rings they contain, and on the basis of structural elements that bind these rings to one another.

Phenolic acid is a type of phytochemical called polyphenol, found in a variety of plant-based foods; the seeds and skins of fruits and the leaves of vegetables contain the highest concentrations. Phenolic acids are readily absorbed through the walls of the intestinal tract, and they may be beneficial to health because they work as antioxidants that prevent cellular damage due to free-radical oxidation reactions. There are many different phenolic acids found in nature, and they can be divided into two categories: benzoic acid derivatives, such as gallic acid; and cinnamic acid derivatives, including caffeic acid and ferulic acid. The cinnamic acids are more common than the benzoic acids.

Flavonoids are the largest family of polyphenolic compounds; they have structure consisting of 2 aromatic rings (A and B) that are bound together by 3 carbon atoms that form an oxygenated heterocycle (ring C). Flavonoids are further divided into 6 subclasses as a function of the type of heterocycle involved: flavonols, flavones, isoflavones, flavanones, anthocyanidins, and flavanols (catechins and proanthocyanidins). Plants produce flavonoids as a protection against parasites, oxidative injury and harsh climatic conditions.

There are three major classes of plant flavonoids (anthocyanins, proanthocyanins, and flavonols), synthesized via the branched flavonoid biosynthetic pathway. Anthocyanins, the most important flavonoid class, are the main pigments in flowers and fruits; these pigments are vital for insect attraction, necessary for pollination and seed dispersal (Winkel-Shirley, "Flavonoid Biosynthesis. A Colorful Model for Genetics, Biochemistry, Cell Biology, and Biotechnology", Plant Physiol. Vol. 126, 2001). The basic anthocyanins consist mainly of pelargonidin, cyanidin, and delphinine; various modifications of these compounds, such as glycosylation, acylation, and methylation may occur, contributing to diversity in flower color (Morata et al., "Formation of the highly stable pyranoanthocyanins (vitamins A and B) in red wines by the addition of pyruvic acid and acetaldehyde", Food Chemistry 100 (2007) 1144-1152). Anthocyanins have been also demonstrated to have a broad spectrum of biological functions and may act as good antioxidant like other members of flavonoids family Flower pigmentation involves a complex multi-enzymatic biosynthetic pathway, in which several enzymatic reactions result in the production and accumulation of flavonoid compounds. Flavonoids play important roles in many biological processes, such as UV protection (Li et al., "Arabidopsis Flavonoid Mutants Are Hypersensitive to UV-6 Irradiation", The Plant Cell, Vol. 5, 171-179, February 1993), pathogen defense (Treutter, "Significance of Flavonoids in Plant Resistance and Enhancement of Their Biosynthesis", Plant Biology 7 (2005) 581-591), and pollen viability (Taylor, L P and Jorgensen R (1992). "Conditional male fertility in chalcone synthase-deficient petunia". J. Hered. 83: 11-17). Peach flower contains particular flavonoids, four kaempferol glycoside derivatives (multiflorin B, trifolin, afzelin, and astragalin) and a skin protection effect was demonstrated for multiflorin B (Young ha Kim et al., "The extract of the flowers of Prunus persica, a new cosmetic ingredient, protects against solar ultraviolet-induced skin damage in vivo", j. Cosmet. Sci., 53, 27-34 (January/February 2002))

Among the "flavonoids" used in the invention, may be mentioned in particular taxifolin, catechin, epicatechin, eriodictyol, naringenin, rutin, troxerutin, chrysin, tangeretin, luteolin, epigallocatechin gallate and epigallocatechin, quercetin, fisetin, kaempferol, galangin, gallocatechin, epicatechin gallate.

(Hassani et al., (2015), "Analysis of biochemical compounds and differentially expressed genes of the anthocyanin biosynthetic pathway in variegated peach flower", Genetic Mol Res. 14(4):13425-36) provides a comparative study by LC-MS analysis of the compounds produced in flower petals of different colors (white and pink) from a marked, variegated peach tree. Several glycosylated derivatives of cyanidin (cyanidin-3-glucoside, cyanidin-3-(6"-malonyl glucoside), cyanidin-3-(6"-ethylmalonyl glucoside)) also pelargonidin (pelargonidin-3-glucoside, Pelargonidin-3-(6"-ethylmalonyl glucoside) and peonidin (peonidin-3-glucoside and Peonidin-3-(6"-ethylmalonyl glucoside)) were detected in pink petal however; none of these compounds were detected in white extracts. These compounds in particular cyanidin have been described for their antioxidant and anti-inflammatory effect as described in the work of Jung et al published in 2014. They have been recognized as having the potential to reduce disease risk, anti-aging effect. The antioxidant effect of pink peach blossom extract has been investigated according to the method of 2,2-Diphenyl-1-picrylhydrazyl (DPPH).

The antioxidant effect of pink peach blossom extract according to the invention has been investigated according to the method of DPPH. DPPH assay is a rapid, simple method to measure antioxidant capacity involving the use of the free radical, 2,2-Diphenyl-1-picrylhydrazyl (DPPH) which is widely used to test the ability of compounds to act as free radical scavengers or hydrogen donors and to evaluate antioxidant activity.

The DPPH assay method is based on the reduction of DPPH, a stable free radical. The free radical DPPH with an odd electron gives a maximum absorption at 515 nm (purple colour). When a solution of DPPH is mixed with a substance that can donate a hydrogen atom, then this gives rise to the reduced form (Diphenylpicrylhydrazine; non radical) with the loss of this violet colour to a residual pale yellow colour from the picryl group still present (Prieto P, Pineda M, and Aguilar M (1999), "Spectrophotometric quantitation of antioxidant capacity through the formation of a phosphomolybdenum complex: Specific application to the determination of vitamin E", Anal Biochem 269, 337-341).

One of the advantages of the present invention is that the pink peach flowers are highly enriched in different compounds of interest compared to leaves, fruits, roots or any other parts of the plant.

The present invention provides a peach flower extract obtained from *Prunus persica* species and more preferably the Peach flower extract is obtained from the whole flower.

According to the invention "whole flower" or "peach flower", comprises both petals and sepals. Flowers maybe either fresh or dried. Preferably, the flowers are dried by natural shadow air drying or at 45° C. for 48 hours or at 15° C. for 72 hours in a hot air oven.

The peach flower extract according to the invention can be obtained by aqueous extraction. A large number of compounds found in peach extract are likely to have biologically activity are water soluble.

In a preferred embodiment, the present invention provides a process for obtaining an extract from peach flower (*Prunus persica L.*), said process comprising:
  (i) adding water to peach flower to make a mixture,
  (ii) agitating the said mixture for 2 hours by maintaining temperature from RT to below 70° C.
  (iii) filtering the mixture to remove the solid flower part to obtain the extract.
  (iv) pasteurizing the mixture overnight at a temperature below 70° C.

Flowers may be either fresh or dried. In a preferred embodiment, flowers are dried and water is added to the dried flowers to make a mixture. Any of the well-known methods of drying, such as natural shadow or oven drying can be performed. In a most preferred embodiment flowers are dried in an oven during 48 h to 72 hours at a temperature of 15° C. to 45° C.

In a preferred embodiment the peach flower material is macerated in water. The solution is subjected to short time gentle maceration for 2 hours at a temperature between RT to less than 70° C. Most preferably the temperature is maintained between RT to 50° C. to preserve the integrity of molecules of interest such as flavonoids and phenolic acids and so their ability to act as antioxidant.

The selection of the extraction temperature depends on the desired type of compounds to be extracted, the structural characteristics of the botanical source (flowers, fruits, stems, seeds, leaves, root), the quality and yield required for the extract, and the economic feasibility for scaling up the process. The extraction of the phenolic compounds from the plant material is influenced by the extraction temperature and time, which reflects the conflicting actions of solubilization and analyte degradation by oxidation. However, many phenolic compounds are easily hydrolyzed and oxidized. Long extraction times and high temperature increase the chance of oxidation of phenolics which decrease the yield of phenolics in the extracts. The analysis was done at different temperatures and showed that high temperatures degrade these types of molecules. The extract has complex structures and with heat they are destructured and lose their potential biological activity. High temperatures have been shown to cause rapid anthocyanin degradation. Indeed long time extraction and high temperature (70° C. and above) increase the chance of oxidation which decrease yield of polyphenolic compounds in the extract, also a pH around 4-5 is suitable for stability of polyphenolic compounds. Therefore, it is of critical importance to select efficient extraction temperature to obtain and maintain the stability of phenolic compounds.

The water extraction can be carried out at room temperature or with water heated at no more than 70° C., while being agitated. Preferably, the extraction is carried out by maceration in water heated at 50° C. for 2 hours. The raw solution is then subjected to grid filtering to remove insoluble material. After grid filtering, the aqueous or liquid fraction is collected. To remove smaller residues of the aqueous extract, a filtration by any process well known by someone skilled in the art may be carried out.

In a preferred embodiment, the purification process begins by successive filtrations using filters with decreasing porosity from 50-20 µm until 0.5-0.2 µm to get an extract. In another preferred embodiment, the extract obtained is composed of protein fragments and peptides with a molecular weight of less than 10 kDa, as demonstrated by sodium dodecyl sulfate polyacrylamide gel electrophoresis (SDS-PAGE). The obtained extract is a clear and brilliant solution.

In another preferred embodiment, the extract is then diluted at a concentration between 8 g/Kg and 13 g/Kg, preferably at 11 g/Kg of dry matter with solvents, such as water, glycerol, ethanol, propanediol, butylene glycol, dipropylene glycol, ethoxylated or propoxylated glycols, cyclic polyols or any mixture of these solvents for example 30% glycerol and 0.85% of phenoxyethanol by maintaining the pH between 4.0 to 4.5.

Then, the diluted active agent is sterilized by sterile filtration Then the solution is heated overnight at 65° C. to perform low-temperature pasteurization.

Furthermore, the diluted active agent according to the invention can be qualitatively and quantitatively analyzed. The characteristics are the following:
  Proteins: 3-6 g/kg,
  Sugars: 3-6 g/kg,
  Amino acids: 0.5-1.5 g/kg, Phenolic compounds: 0.5-1.5 g/kg,
Flavonoids: 0.1-0.4 g/kg.

The extract does not contain any ceramide or sphingolipid.

Protein contents of the peach flower extract have been determined by Lowry protein assay (Lowry O H, Rosebrough N J, Farr A L, Randall R J (1951). "Protein measurement with the Folin phenol reagent", J. Biol. Chem. 193 (1): 265-75) which has been used to quantify total protein content of the extract. The Lowry assay is a biochemical assay for determining the total level of protein in a solution. The Lowry method is based on the reaction of Cu+, produced by the oxidation of peptide bonds, with Folin-Ciocalteu reagent. The absorbance of the sample is read on the spectrophotometer at 550 nm. The protein content is determined using a BSA standard curve.

Aminoacid content of the peach flower extract have been determined starting from a protocol published by Moore et al. (Moore et al, "Photometric ninhydrin method for use in the chromatography of amino acids", Journal of Biological Chemistry 1948 Vol. 176 pp. 367-388). The free amino acid content of the extract was assessed by the formation of a colored complex, following the rupture of the amine and carboxylic functions by the reagent ninhydrin. The absorbance of the complex is read on the spectrophotometer at 570 nm. The total amino acids content is determined using a standard curve of amino acids pool.

Total sugars content on the peach flower extract was determined colorimetrically via an adaptation of the assay described by (Dubois et al. ("Colorimetric Method for Determination of Sugars and Related Substances", Anal. Chem., 1956, 28 (3), 350-356). This analysis consists in concentrated sulfuric acid reacting with phenol to form a colored complex. The absorbance of the complex is read on the spectrophotometer at 490 nm. The sugar content is determined using a glucose standard curve.

Polyphenols content of the peach flower extract was determined using the Folin-Ciocalteu assay (Singleton et al. (1999). "Analysis of total phenols and other oxidation substrates and antioxidants by means of Folin-Ciocalteu reagent", 299: 152). Polyphenols compounds in the sample react with the Folin-Ciocalteu reagent, the oxidation of the reagent give a blue color. The absorbance of the sample is read on the spectrophotometer at 760 nm. The content was expressed as gallic acid equivalents using a gallic acid standard curve.

SDS PAGE electrophoresis was performed to assess molecular weight of proteins of the extract. The peach flower extract is heated to 70° C. for 10 minutes in reductive denaturing conditions in a denaturing sample buffer. An antioxidant solution is added to the inner chamber (cathode) so that the reduced proteins do not re-oxidize during electrophoresis. Protein migration is carried out using the MES running buffer with standard Novex® Sharp as a marker for molecular weight. Protein staining is carried out using silver staining.

The advantage of the extract according to the invention is that small compounds are more stable and reproducible without having an allergenic effect.

In another aspect, the present application provides a cosmetic composition comprising peach flower extract obtained by aqueous extraction, wherein the peach flower extract comprises compounds having a molecular weight of less than 10 kDa and a physiologically acceptable medium.

In another preferred embodiment, the peach flower extract is present in a concentration range from about 0.0001% to about 20% by weight, preferably 0.0005% to about 5% by weight of the total weight of the composition.

In another embodiment, the peach flower extract is used for cosmetic applications, more preferably for topical applications.

In another preferred embodiment, the present invention provides oral, parenteral or topical formulations adapted by the person skilled in the art, in particular for cosmetic or dermatological compositions. The compositions according to the invention are advantageously designed to be administered topically. These compositions must therefore contain a physiologically acceptable medium, i.e. compatible with the skin and epithelial appendages, and cover all cosmetic or dermatological forms.

Further, the present compositions preferably are in the form of an aqueous, hydroalcoholic or oily solution; oil-in-water emulsion, water-in-oil emulsion or multiple emulsions; creams, suspensions, powders adapted for application on the skin, mucus membranes, lips and/or epithelial appendages. These compositions can also be more or less fluid and have the appearance of a cream, a lotion, milk, a serum, pomade, a gel, a paste or a mousse. They can also exist in solid form, as a stick, or can be applied to the skin as an aerosol. They can also be used as a skincare product and/or as a makeup product.

In another embodiment, the composition comprises conventionally used additive envisaged in the scope of application as well as necessary additives for their formulation, such as co-solvents (ethanol, glycerol, benzyl alcohol, damper . . . ), thickeners, thinners, emulsifiers, antioxidants, colorants, solar filters, pigments, fillers, preservatives, perfumes, odor absorbers, essential oils, oligo elements, essential fatty acids, surfactants, film-forming polymers, chemical filters or minerals, moisturizing agents or thermal waters etc. Water-soluble, preferably natural, polymers, such as polysaccharides or polypeptides, cellulose derivatives of the type methylcellulose or hydroxypropylcellulose, or even synthetic polymers, poloxamers, carbomers, siloxanes, PVA or PVP, and in particular polymers sold by the company Ashland, can be cited, for example.

It is well understood that the active agent according to the invention can be used on its own or in conjunction with other active ingredients.

Furthermore, the compositions which can be used according to the invention advantageously contain at least one other active agent. The following types of ingredients can be cited, in a non-limiting manner: other peptide active agents, vegetable extracts, healing agents, anti-aging agents, anti-wrinkle agents, soothing agents, anti-free radicals, anti-ultraviolet radiation agents, agents for stimulating dermal macromolecular synthesis or energetic metabolism, moisturizing agents, antibacterial agents, antifungal agents, anti-inflammatories, anesthetics, agents modulating cutaneous differentiation, cutaneous pigmentation or depigmentation, and agents for stimulating nail and hair growth.

It is preferable for an anti-free radical or antioxidant agent, or an agent stimulating dermal macromolecular synthesis or energetic metabolism, to be used.

In a more specific embodiment, the composition according to the invention will comprise:
Sunscreens, ultraviolet and Infra-red screens
Anti-free radical agents,
DHEA (dehydroepiandrosterone),
At least one cytochrome co-activating compound, and/or;
One (or more) aquaporin-activating compound and/or;
One (or more) sirtuin-activating compound and/or;

One (or more) compound that increases cell adhesion and/or;
One (or more) compound that increases the production of matrix proteins of the collagen or laminin type, etc.;
One (or more) HSP protein-modulating compound;
One (or more) compound that increases cell energy;
One (or more) pigmentation-modulating compound such as a yeast, amaranth, linseed, bean, cacao, corn, soy, sunflower, rapeseed or pea peptide extract;
One (or more) compound improving the skin barrier function;
One (or more) mitochondria-protecting compound.
Vitamin A and notably retinoic acid, retinol, retinol proprionate, retinol palmitate,
Vitamin B3 and notably niacinamide, niconitate of tocopherol,
Vitamin B5, vitamin B6, vitamin B12, panthenol,
Vitamin C, and notably ascorbic acid, ascorbyl glucoside, ascorbyl tetrapalmitate, magnesium and sodium ascorbyl phosphate,
Vitamins E, F, H, K, PP, and coenzyme Q10, Metalloproteinase inhibitor, activator of Tissue Inhibitor Metalloproteinase (TIMP),
Aminoacids and notably arginine, ornithine, hydroxyproline, hydroxyproline dipalmitate, palmitoylglycine, hydroxylysine, methionine and its derivatives, N-acylated aminoacids,
Natural or synthetic peptides, including, di-, tri-, tetra-, penta- and hexapeptides and their lipophilic derivatives, isomers and complex with other molecules such as metallic ion (i.e. copper, zinc, manganese, magnesium, and others), peptides sold under commercial names MATRIXYL®, ARGIRELINE®, CHRONOGEN™, LAMINIXYL IS™, PEPTIDE Q10™, COLLAXYL™ (patent FR2827170, ASHLAND®), PEPTIDE VINCI 01™ (patent FK2837098, ASHLAND®), PEPTIDE VINCI 02™ (patent FR2841781, ASHLAND®), ATPeptide™ (patent FR2846883, ASHLAND®) or synthetic peptide of sequence Arg-Gly-Ser-NH2, sold under commercial name of ATPeptide™ by ASHLAND®;
Extract of Artémia salina, sold under commercial name of GP4G™ (FR2817748, ASHLAND®);
Botanical peptide extracts such as flaxseed extract (Lipigénine™, patent FR2956818, ASHLAND®), soya extract, einkorn, grapevine, rapeseed, rice, corn or pea;
Yeast extracts, such as Dynagen™, (patent FR2951946, ASHLAND®) or Actopontine™ (patent FR2944526, ASHLAND®); dehydroacetic acid (DHA),
Natural or synthetic phystosterols,
alpha- and beta-hydroxyacids, silanols,
Sugar amines, glucosamine, D-glucosamine, N-acetyl-glucosamine, N-acetyl-D-glucosamine, mannosamine, N-acetyl mannosamine, galactosamine, N-acetyl galactosamine,
Polyphenols, isoflavones, flavonoids, such as grape extract, pine extract, olive extract,
Lipids such as ceramides or phospholipids,
Animal oils such as squalenes or squalanes,
Vegetal oils, such as almond oil, coconut oil, castor oil, jojoba oil, olive oil, rapeseed oil, peanut oil, sunflower oil, wheat germ oil, corn germ oil, soybean oil, cotton oil, alfalfa oil, poppy oil, pumpkin seed oil, evening primrose oil, millet oil, barley oil, rye oil, safflower oil, passion oil, hazelnut oil, palm oil, apricot kernel oil, avocado oil, calendula oil, ethoxylated vegetable oils, or shea butter, the above mentioned compounds can be natural, such as peptide hydrolysates of plants, or also synthetic, such as peptide compounds.

In yet another embodiment, the present application provides a cosmetic method for reducing and/or correcting the signs of aging and photo-aging of the skin and keratinous appendages, comprising topically applying to the skin, the mucous membranes and/or skin appendages a composition comprising a peach flower extract according to the application.

It is clear that the invention is designed for mammals in general, and more specifically for human beings. The inventors have indeed identified biological activities which are useful to reduce and/or correct the cutaneous signs of aging and photo-aging of the skin and keratinous appendages, and to protect the skin against aggressions due to ultraviolet radiation.

"Cutaneous signs of aging and photo-aging" refers to all changes in the external appearance of the skin and skin appendages due to aging, such as, for example, thinning of the skin, sagging, loss of hydration and atonia, deep wrinkles and fine lines, loss of firmness and tone, dermal atrophy or any other internal degradation of the skin resulting from exposure to ultraviolet radiation, liver spots and age spots.

In yet another aspect, the present application provides a cosmetic method to protect the skin against aggressions due to ultraviolet radiation, wherein a cosmetic composition comprising a peach flower extract according to the invention is applied topically on the skin which is to be treated.

In yet another embodiment, the present application provides a cosmetic method to modulate the SIRT2 expression in skin cells, wherein a cosmetic composition comprising a peach flower extract according to the invention is applied topically on the skin which is to be treated.

The embodiments which are specific to this cosmetic method also result from the above description.

Further advantages and characteristics of the invention can be seen in greater detail by reading the illustrative, non-limiting examples provided.

EXAMPLE 1

Preparation of a Peach Flower Extract (*Prunus Persica L.*)

The pink peach flowers were obtained from Damyang, South Jeolla, South Korea. The flowers were dried by natural shadow air drying or at 45° C. for 48 hours or at 15° C. for 72 hours in a hot air oven. 50 g of dry peach flower (*Prunus persica*) were placed in 1 liter of distilled water. The solution was heated 2 hours at a temperature of 50° C. Then a filter grid was used to separate solid flower residue from the liquid part—The purification process begins by successive filtrations using filters of decreasing porosity (from 0.5 to 0.2 µm) so as to obtain a clear, bright solution. The filtrate was then diluted to obtain an extract having between 10-12 g/Kg dry matter with 30% glycerol and 0.85% phenoxyethanol. The pH of the solution was adjusted between 4 and 5, to increase the stability of the extract. After clarification and dilution, the filtrate was then filter-sterilized with 0.2 µm filter porosity under sterile condition. Then the solution was heated overnight at 65° C. to perform low-temperature pasteurization. Peach flower extract was analyzed using standard procedure. The characteristics of the peach flower extract obtained are the following: dry matter: 11 g/kg—proteins: 4.5 g/kg—sugars: 4.5 g/kg—amino acids: 0.7 g/kg and polyphenolic compounds: 1.1 g/Kg. Methods used in spectrophotometry assay to determine the amount of different compounds in the peach flower extract: Proteins content of the peach flower extract have been determined by Lowry protein assay (Lowry et al, 1951) to quantify total protein content of the extract. The Lowry assay is a biochemical assay for determining the total level of protein in a solution. The Lowry method is based on the reaction of Cu+, produced by the oxidation of peptide bonds, with Folin-Ciocalteu reagent. The absorbance of the sample is read on the spectrophotometer at 550 nm. The protein content was determined using a BSA standard curve. Aminoacid content of the extract have been determined starting from a protocol published by Moore et al (1948), the free amino acid content of the extract was assessed by the formation of a colored complex, following the rupture of the amine and carboxylic functions by the reagent ninhydrin. The absorbance of the complex is read on the spectrophotometer at 570 nm. The total amino acids content was determined using a standard curve of amino acids pool.

Total sugar content on the extract was determined colorimetrically via an adaptation of the assay described by Dubois et al (1956) (Dubois et al, "Colorimetric Method for Determination of Sugars and Related Substances", Anal. Chem., 1956, 28 (3), 350-356). This analysis consists in the dissolution of the raw material in concentrated sulfuric acid and then reacting with phenol to form a colored complex. The absorbance of the complex is read on the spectrophotometer at 490 nm. The sugar content is determined using a glucose standard curve.

Polyphenol content of the peach flower extract was determined using the Folin-Ciocalteu assay (Singleton et al., "Analysis of total phenols and other oxidation substrates and antioxidants by means of Folin-Ciocalteu reagent", 1999, 299: 152). Polyphenol compounds in the sample react with the Folin-Ciocalteu reagent, the oxidation of the reagent gives a blue color. The absorbance of the sample is read on the spectrophotometer at 760 nm. The content was expressed as gallic acid equivalents using a gallic acid standard curve SDS PAGE electrophoresis was performed to assess molecular weight of proteins of the extract. The peach flower extract is heated to 70° C. for 10 minutes in reductive denaturing conditions in a denaturing sample buffer. An Antioxidant solution is added to the inner chamber (cathode) so that the reduced proteins do not re-oxidize during electrophoresis. Protein migration is carried out using the MES running buffer with standard Novex® Sharp as a marker for molecular weight. Protein staining is carried out using silver staining.

The extract obtained is composed of peptides with a molecular weight of less than 10 kDa.

HPLC Protocol

Chromatographic Analysis of Phenolic Acids:

All samples were separated on a Column Uptisphere CS evolution 100 mm×4.6 mm×2.6 µm (ref Interchim: UE2.6AQ-100/046) by an Agilent 1260 HPLC system (Agilent Technologies, Calif., USA). The flow rate was 0.8 ml min-1. The mobile phase consisted of 0.1% TFA (Trifluoroacetic acids) in aqueous solution (A) and methanol (B). The elution was facilitated by gradient program as follows (see table):

TABLE 1

Gradient of Elution

| Time (min) | Eau/TFA a 0.1% (%) | Methanol (%) |
|---|---|---|
| 0 | 100 | 0 |
| 7 | 82 | 18 |
| 30 | 78 | 22 |
| 35 | 5 | 95 |
| 40 | 5 | 95 |
| 42 | 95 | 5 |

The column temperature was maintained at 25° C. The injection volume was 20 µL and the detection wavelength was set at 280 nm using a UV detector Amino acids standards were purchased from Sigma-Aldrich. Identification of amino acids was performed by comparison of retention times and UV spectral peaks of the sample with authentic standard. Quantitative estimation of phenolic acids was done based on the peak area of the sample concentrations and standard.

Chromatographic Analysis of Amino Acids:

All samples were separated on a Column Uptisphere Strategy C18-2 5 µm (250×4.6 mm) US5C182-250/046 (ref Interchim: UE2.6AQ-100/046) by an Agilent 1260 HPLC system (Agilent Technologies, Calif., USA). The flow rate was 1 ml/min. The mobile phase consisted of phosphoric acid (H3PO4) 0.1% solution (A) and acetonitrile (B). The elution was facilitated by gradient program as follows (see table):

TABLE 2

Gradient of Elution

| Time (min) | H3PO4(0.1%) | Acetonitrile (ACN) (%) |
|---|---|---|
| 0 | 87 | 13 |
| 20 | 54 | 46 |
| 22 | 54 | 46 |
| 27 | 60 | 40 |
| 30 | 60 | 40 |
| 35 | 5 | 95 |
| 37 | 87 | 13 |

The column temperature was maintained at 25° C. The injection volume was 5 µL and the detection wavelength was set at 254 nm using a UV detector Amino acids standards were purchased from Sigma-Aldrich. Standard and sample before injection are derivatized with phenylisothiocyanate (PITC). Identification of amino acids was performed by comparison of retention times and UV spectral peaks of the sample with authentic standard. Quantitative estimation of amino acids was done based on the peak area of the sample concentrations and standard.

HPLC Analysis

TABLE 3

HPLC analysis

| Process (T° C.) | Total amount of Phenolic acid (mg/Kg) | Chlorogenic acid content (mg/kg) |
|---|---|---|
| RT | 534 | 422 |
| 50° C. | 478 | 342 |
| 70° C. | 266 | 220 |

TABLE 4

HPLC analysis - Results at a temperature of 50° C. & 70° C.

| Process T° C. | Dry matter (g/kg) | Amino acids (mg/Kg) -HPLC | Phenolic acid (mg/Kg) - HPLC | Catechin content (mg/Kg) - HPLC |
|---|---|---|---|---|
| 50° C. | 15.3 | 1432 | 494 | 156 |
| 70° C. | 15.3 | 1304 | 214 | 22 |

It was observed that the catechin content is very low at 70° C. compared to 50° C., Catechin belongs to the group of flavonols, part of the chemical family of flavonoids that is a type of natural phenol and is a potent antioxidant molecule. The decreasing content of this molecule with rising temperature may explain the fact that the extract obtained 70° C. are less antioxidant than the extract obtained at a lower temperature.

As a conclusion it has been shown that an extraction performed at 50° C. preserves specifically catechin molecules.

EXAMPLE 2

SIRT2 mRNA Study on Keratinocytes and Fibroblasts Treated with Peach Flower Extract of Example 1, by qPCR The object of this study is to determine the influence of peach flower extract of example 1 on Sirtuin 2 mRNA level in human cells, by qPCR.

Protocol:

Treatment solution of synthetic SIRT2 peptide was prepared by diluting a stock solution of 100 ppm ("ppm" refers to parts per million) in the culture medium of the cells at 0.5% vol/vol.

Treatment solution of peach flower extract were prepared by diluting peach flower extract of example 1 at 0.1% vol/vol, or a 0.5% vol/vol, in the culture medium of the cells.

Normal human keratinocytes or normal human fibroblasts were treated twice with a solution of 0.5% vol/vol, of a synthetic SIRT2 activating peptide or with 0.1% vol/vol or 0.5% vol/vol of peach flower extract of example 1 for 24 hours. Total RNA was first extracted using the RNeasy Mini Kit (74106, Qiagen); then, total RNA was reverse-transcribed with the High Capacity cDNA Reverse Transcription Kit (4374966, Life technologies). Finally, real-time PCR was performed on a thermocycler (Applied Biosystems) with TaqMan Gene Expression Master Mix (4369514, Life technologies) and TaqMan Gene Expression Assays (Hs00247263_m1, Life technologies) which were composed of two primers and one probe specific of the sequence. 18S TaqMan Gene Expression Assay (Hs99999901_s1, Life technologies) was used as endogenous control and the comparative Ct method was used for relative quantification of target expressions.

Results:

The SIRT2 mRNA level was increased after the treatment with the peach flower extract both on keratinocytes and fibroblasts, compared to untreated cells. The level was high and significantly (Student's t test) increased by 64% and 56% after 0.1% treatment and by 88% and 91% after 0.5% treatment on keratinocytes and fibroblasts respectively.

Figure 2:
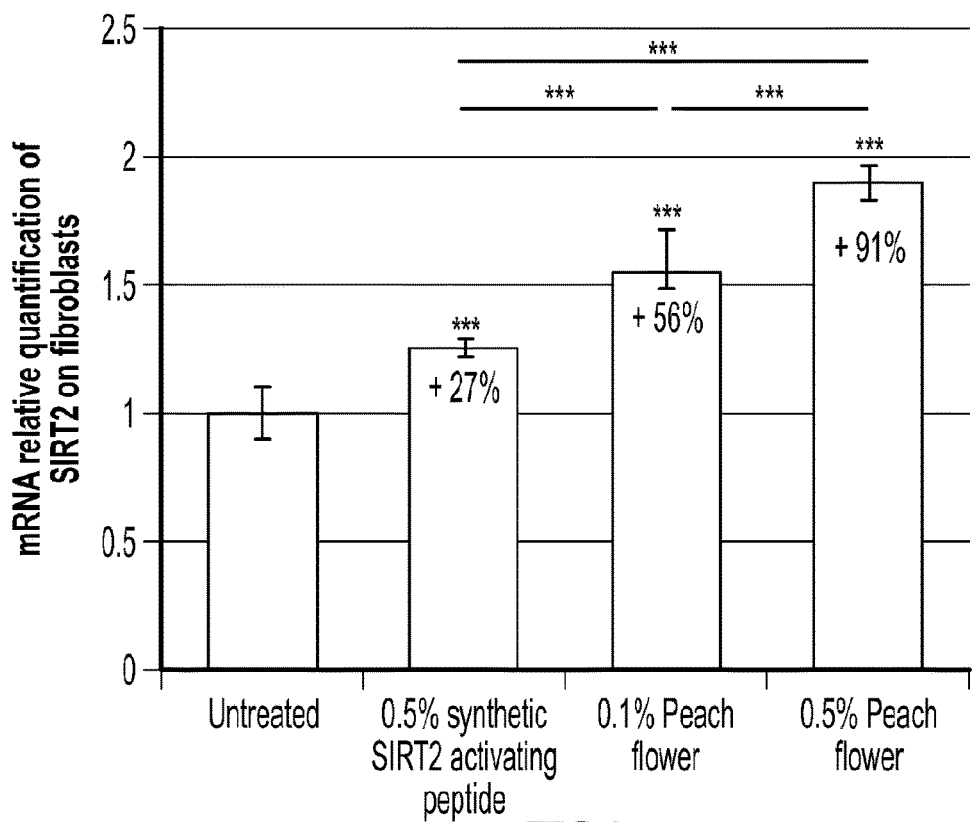
FIG. 2 is illustration of quantification of SIRT2 mRNA study on fibroblasts

Conclusion:

The level of SIRT2 mRNA was quantitatively increased in cells treated with the peach flower extract for 24 hours. Results are illustrated in FIG. 1 & FIG. 2

TABLE 5

SIRT2 mRNA Expression on Keratinocytes & Fibroblasts after treatment with peach flower extract

| | Method | Synthetic SIRT2 activating peptide | Peach flower extract (0.1%) | Peach flower extract (0.5%) |
|---|---|---|---|---|
| Keratinocytes | qPCR | +12%*** | +64%*** | +88%*** |
| Fibroblasts | qPCR | +27%*** | +56%*** | +91%*** |

EXAMPLE 3

SIRT2 Protein Expression Study on Keratinocytes Treated with Peach Flower Extract of Example 1

The object of this study is to determine the influence of peach flower extract of example 1 on Sirtuin 2 protein expression on cells. To do this, specific labeling by immunofluorescence was carried out on normal human keratinocytes.

Protocol:

Treatment solution of peach flower extract were prepared as in example 2.

Normal human keratinocytes were treated twice with a solution of 0.5% of a synthetic SIRT2 activating peptide or with 0.1% vol/vol or 0.5% vol/vol of peach flower extract of example 1 for 24 hours. For immunolabelling by anti-SIRT2 antibody, the cells were washed and fixed with paraformaldehyde at 3.7% for 10 minutes. The cells were then incubated in the presence of a specific anti-SIRT2 antibody (Abcam, ref. ab19388, rabbit polyclonal), and then a secondary suitable antibody, coupled with a fluorescent dye. After mounting in a particular medium, the slides were observed by epifluorescence microscope (Nikon Eclipse 80i microscope).

Results:

Microscopic observation showed an increased SIRT2 staining on keratinocytes, after the treatment with the peach flower extract.

Conclusion:

The expression of SIRT2 protein was visually increased in cells treated with the peach flower extract for 24 hours.

EXAMPLE 4

SIRT2 Protein Expression Study on Ex Vivo Human Skin Biopsies Treated with Peach Flower Extract of Example 1

The object of this study is to determine the influence of peach flower extract of example 1 on Sirtuin 2 protein expression on skin. To do this, specific labeling by immunofluorescence was carried out on normal human skin biopsies.

Protocol:

Treatment solution of peach flower extract were prepared as in example 2.

Normal human skin biopsies were treated twice with a solution of 0.1% vol/vol or 0.5% vol/vol of peach flower extract of example 1 for 24 hours. For immunolabelling by anti-SIRT2 antibody, tissues were fixed and embedded in paraffin. Embedded skin biopsies were then cut and sections were deparaffinized and rehydrated. Then, an unmasking protocol was performed before applying a specific anti- SIRT2 antibody (Abcam, ref. ab19388, rabbit polyclonal), and then a secondary suitable antibody, coupled with a fluorescent dye. After mounting in a particular medium, the slides were observed by epifluorescence microscope (Nikon Eclipse 80i microscope).

Results:

Microscopic observation of SIRT2 immunofluorescent staining on skin sections showed an increase of SIRT2 expression after the treatment with the peach flower extract, in a dose dependent manner, as shown in table 5. The increase was in a dose-dependent manner and higher in comparison to the treatment with the synthetic peptide.

Conclusion:

The expression of SIRT2 protein was visually increased in skin biopsies treated with the peach flower extract for 24 hours.

EXAMPLE 5

BubR1 mRNA Study on Keratinocytes Treated with Peach Flower Extract of Example 1, by qPCR As BubR1 protein is under control of SIRT2 and is linked to mammalian aging, the object of this study is to determine the influence of peach flower extract of example 1 on BubR1 mRNA level in human cells, by qPCR.

Protocol:

Treatment solution of peach flower extract were prepared as in example 2.

Normal human keratinocytes were treated twice per day with a solution of 0.1% vol/vol or 0.5% vol/vol of peach flower extract of example 1 for 24 hours. Total RNA was first extracted using the RNeasy Mini Kit (74106, Qiagen); then, total RNA was reverse-transcribed with the High Capacity cDNA Reverse Transcription Kit (4374966, Life technologies). Finally, real-time PCR was performed on a thermocycler (Applied Biosystems) with TaqMan Gene Expression Master Mix (4369514, Life technologies) and TaqMan Gene Expression Assays (Hs01084828_m1, Life technologies) which were composed of two primers and one probe specific of the sequence. 18S TaqMan Gene Expression Assay (Hs99999901_s1, Life technologies) was used as endogenous control and the comparative Ct method was used for relative quantification of target expressions.

Figure 3:
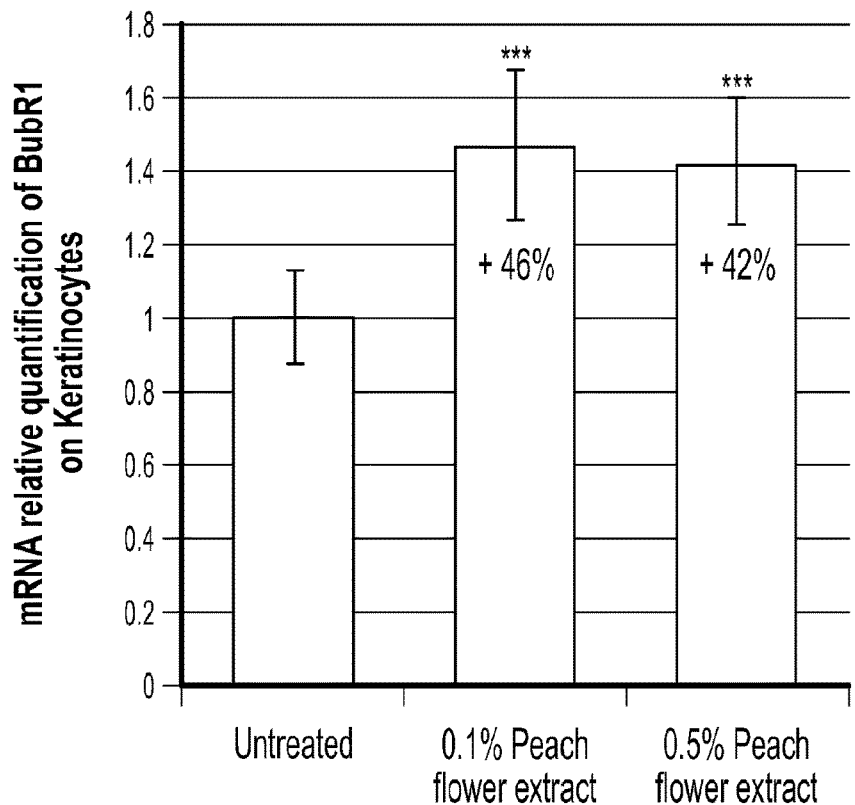
FIG. 3 is illustration of quantification of BubR1 mRNA study on keratinocytes

Results:

The BubR1 mRNA level was increased after the treatment with the peach flower extract on keratinocytes, compared to untreated cells. The level was highly significantly (Student's t test) increased by 46% after 0.1% treatment and by 42% after 0.5% treatment on keratinocytes. The results are illustrated in FIG. 3.

Conclusion:

The level of BubR1 mRNA was increased in keratinocytes treated with the peach flower extract for 24 hours.

EXAMPLE 6

BubR1 Protein Expression Study on Keratinocytes and Fibroblasts Treated with Peach Flower Extract of Example 1

The object of this study is to determine the influence of peach flower extract of example 1 on BubR1 protein expression on cells. To do this, specific labeling by immunofluorescence was carried out on normal human keratinocytes and fibroblasts.

Protocol:

Treatment solution of peach flower extract were prepared as in example 2.

Normal human keratinocytes and normal human fibroblasts were treated twice with a solution of 0.1% vol/vol or 0.5% vol/vol of peach flower extract of example 1 for 24 hours. For immunolabelling by anti-BubR1 antibody, the cells were washed and fixed with paraformaldehyde at 3.7% for 10 minutes. The cells were then incubated in the presence of a specific anti-BubR1 antibody (Abcam, ref. ab4639, mouse monoclonal), and then a secondary suitable antibody, coupled with a fluorescent dye. After mounting in a particular medium, the slides were observed by epifluorescence microscope (Nikon Eclipse 80i microscope). Fluorescence intensity was quantified by analyzing the image using Volocity 6.3. software.

Figure 4:
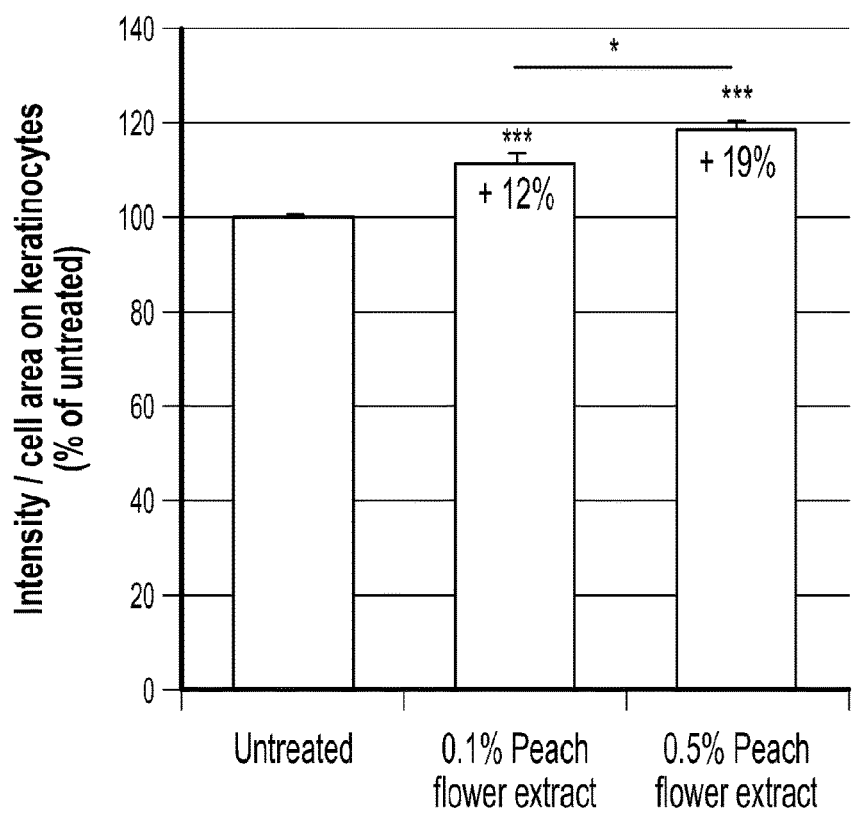
FIG. 4 is illustration of Senescent associated beta-galactosidase (SA beta-gal) activity study on fibroblasts
Figure 5:
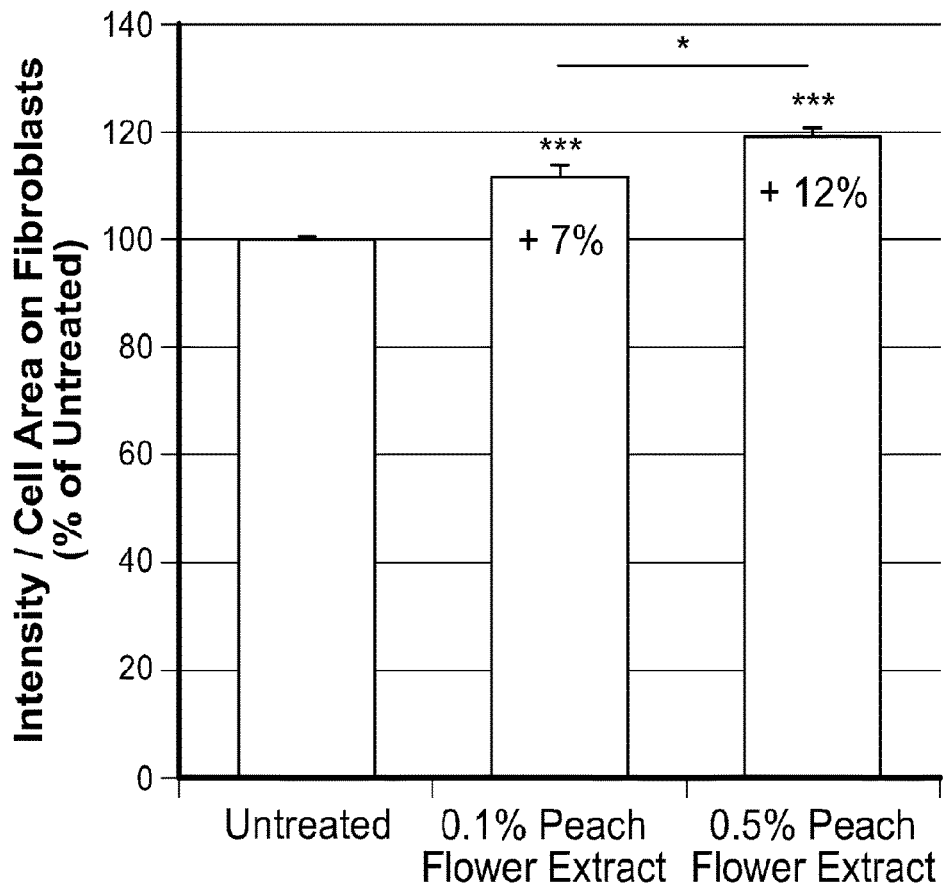
FIG. 5 is illustration of microscopic observation of BubR1 staining on fibroblasts

Results:

Microscopic observation showed a significantly highly (Student's t test) increase in BubR1 staining on keratinocytes and fibroblasts, after the treatment with the peach flower extract. The results are illustrated in FIGS. 4 and 5, respectively.

TABLE 6

Quantification of the microscopic observations of BubR1 Expression on Keratinocytes & Fibroblasts

|  | Untreated | Peach flower extract (0.1%) | Peach flower extract (0.5%) |
| --- | --- | --- | --- |
| BubR1 expression on keratinocytes (intensity/cell area (%)) | 100 | 112*** | 119*** |
| BubR1 expression on fibroblast (intensity/cell area (%)) | 100 | 107*** | 112*** |

Conclusion:

The expression of BubR1 protein was increased in cells treated with the peach flower extract for 24 hours.

EXAMPLE 7

Senescent Associated Beta-Galactosidase (SA Beta-Gal) Activity Study on Fibroblasts Treated with Peach Flower Extract of Example 1

The object of this study is to determine the influence of peach flower extract of example 1 on the beta-galactosidase senescent marker on cells, after a longer application time.

Protocol:

Treatment solution of peach flower extract were prepared as in example 2.

Normal human fibroblasts were treated twice per day with a solution of 0.1% vol/vol or 0.5% vol/vol of peach flower extract of example 1, for 12 sub-cultures (P3 to P15) and compared to untreated fibroblasts at P5. For SA beta-gal activity staining, the cells were first washed and fixed. They were then incubated overnight with SA beta-gal stain solution. After mounting in a particular medium, the slides were observed by light microscopy (Nikon Eclipse E600 microscope). Blue intensity was quantified by analyzing the image using Volocity 6.3. software. A normalization by the number of cells was performed.

Results:

As expected, blue staining increased between untreated "young" fibroblasts (P5) and untreated senescent fibroblasts (P15). This increase was statistical and significantly (Student's test) reduced by 17% and 21% when fibroblasts were treated with the peach flower extract at 0.1% and 0.5% respectively.

Figure 6:
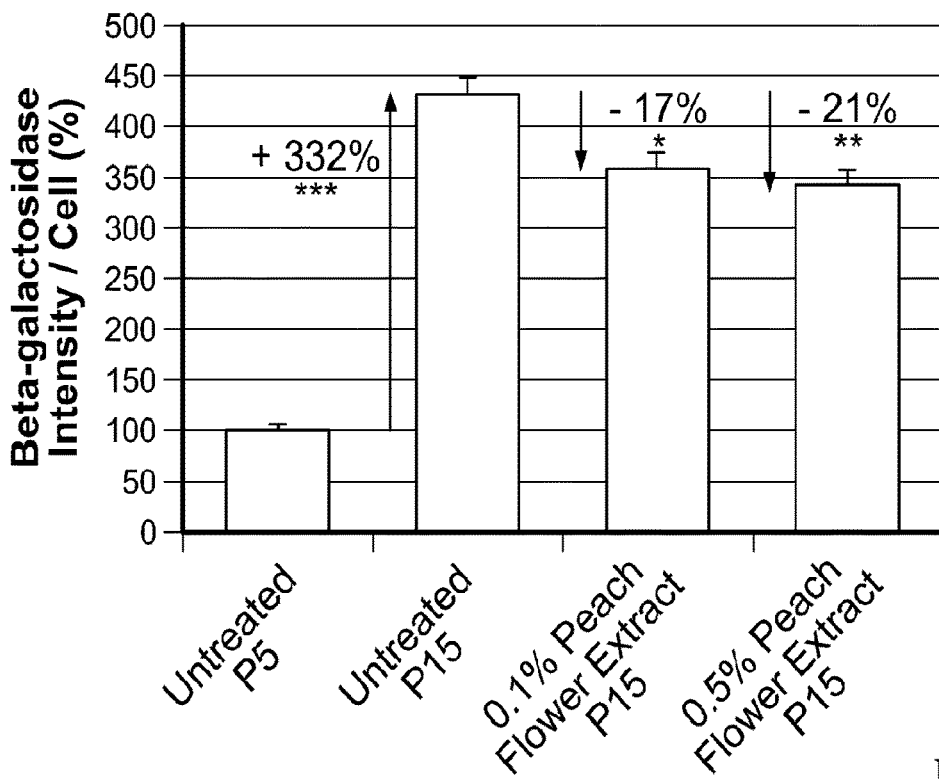
FIG. 6 is illustration of the activity of beta-galactosidase senescent marker on fibroblasts

Conclusion:

The activity of beta-galactosidase senescent marker was decreased in fibroblasts treated with the peach flower extract for long term. The results are illustrated in FIG. 6. While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

EXAMPLE 8

SIRT2 Activation Study on Dermal Fibroblasts Treated with Peach Flower Extract of Example 1

The object of this study is to determine the influence of peach flower extract on Sirtuin 2 cellular migration in human dermal fibroblasts cells, the testing was performed using extract of example 1.

Protocol:

Treatment solution of peach flower extract were prepared by diluting peach flower extract of example 1 at 0.2% vol/vol, 0.5% vol/vol or 1% vol/vol.

Oris Migration Assay

Materials

Oris 96 Well Cell Migration Assay System Collagen I Coated (1-pack), Cat # CMACC1.101
Cell Stain:
  CellTracker Green Life Technologies 1 mg, Cat # C2925
Trypsin:
  Trypsin EDTA 1× Corning, Cat #25-053-CI
Wash:
  Dulbecco's Phosphate Buffered Saline Solution (DPBS) 1×, Cat #25-055-CV
Media:
  Dulbecco's Modified Eagle Media (DMEM) by Life Technologies, Cat #11965092
    With and without supplementation
    For the supplemented media, media was supplemented with:
      Hyclone Fetal Bovine Serum (FBS)@ 10%, Cat # SH30071.03

Samples Tested

1. Control:
  Media Only
2. Migration Positive Control:
  PDGF @ 10 ng/ml Sigma Cat # P8147 Lot # SLBN0763V
3. CR14031 without preservative "Peach Extract" (refers to peach flower extract obtained from Example 1)
  Manuf: Ashland Vincience
  Code: 865810
  Former Code: CR14031
  Batch # RM15048
  0.2% (v/v)
  0.5% (v/v)
  1% (v/v)

Methods

Day 1: Cell Seeding of the Oris Migration Plate and Pre-Treatment with Active:

Oris Cell Migration assay was removed from 4° C. refrigeration prior to seeding in order to allow the plate to come to room temperature.

Under sterile cell culture conditions, the Oris migration plate was seeded with 62-year-old passage 11 Normal Dermal Human Fibroblasts (NHDF's) from Zen Bio Lot # DFM110210B at a density of 20,000 cells per well in 50 ul media per well.

Then, an equal volume (50 ul) of 2× concentrated treatment in media was added to the designated wells, according to the following plate layout (n=10), for a final volume in the well of 100 ul with a resulting 1× treatment. The plate was incubated for 24 hours under standard cell culture conditions of 95% Humidity, 5% $CO_2$ and 37° C.

Shaded wells not utilized and was excess.

TABLE 7

Schema of plate design for the experiment

| | 1 | 2 | 3 | 4 | 5 | 6 | 7 | 8 | 9 | 10 | 11 | 12 |
|---|---|---|---|---|---|---|---|---|---|---|---|---|
| A | | | | | | | Blank | | | | | |
| B | | | | | | | Media | | | | | |
| C | | | | | | | PDGF | | | | | |
| D | | | | | | | Peach 0.2% | | | | | |
| E | | | | | | | Peach 0.5% | | | | | |
| F | | | | | | | Peach 1% | | | | | |
| G | | | | | | | | | | | | |
| H | | | | | | | | | | | | |

Day 2: Stain cells, Refresh Treatment with Active, Start of Migration Assay time points.

The following day, the media and treatments were removed from the plate, the adherent cells were washed twice in 37° C. warm Dulbecco's PBS to wash the cells prior to staining.

Cells were stained using a 10 mM solution of Cell Tracker Green in serum-free media, and incubated for 30 minutes under standard cell culture conditions.

At the end of the 30 min staining, the specialized well inserts in the Oris Migration assay were removed using the tool provided, and the CellTracker Green stain was removed.

The cells were washed twice with pre warmed 37° C. Dulbecco's PBS to clean away any disturbed cells and remaining dye.

1× prepared treatments were refreshed in the plate according to the provided plate layout and the plate was immediately read using a fluorescent plate reader at the following settings: 492 nm ex/517 nm em at the start of the assay designated t=0. Additional time points at 1, 2, 3, 4, 6, 8, and 24 hours were taken and data recorded.

Results:

The results show that the treatment with the peach flower extract increased the cellular migration in 62 yr-old human dermal fibroblast cells and was concentration dependent. Results are reported on table:

TABLE 8

Cellular migration in human dermal fibroblast cells treated with peach flower extract

| | | % Change as compared to the media control | | | | | | |
|---|---|---|---|---|---|---|---|---|
| | | 1 | 2 | 3 | 4 | 6 | 8 | 24 |
| Peach flower extract | 0.2% | 2.21 | 1.37 | 1.81 | 2.33 | 1.96 | 1.66 | 2.63 |
| | 0.50% | 9.04 | 3.64 | 3.59 | 3.65 | 3.53 | 2.99 | 3.82 |
| | 1% | * | * | * | * | * | * | * |
| | | 10.53 | 9.41 | 8.31 | 8.66 | 8.75 | 7.93 | 8.17 |

Conclusion:

By supporting Sirt2 through the peach flower extract, we were able to help cells to regain cellular migration activity in mature skin cells.

Figure 7:
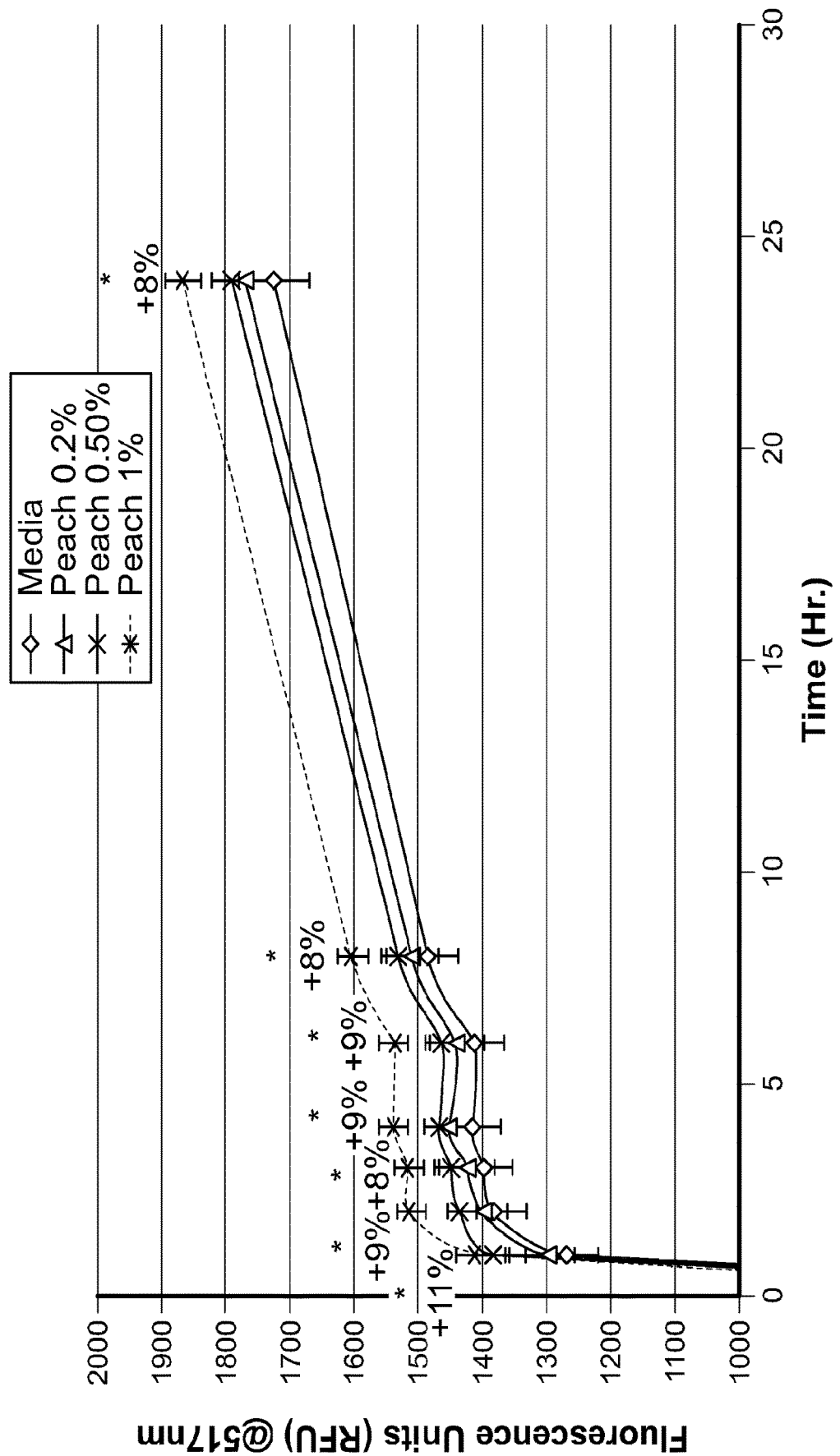
FIG. 7 is illustration of quantification of fibroblasts through a fluorescent marker system

The results are illustrated in FIG. 7.

EXAMPLE 9

Measurement of Average Cell Number after Treatment with Peach Flower Extract of Example 1

The object of this study is to determine the influence of peach flower extract on average cell number, the testing was performed using extract of example 1.

Protocol:

Treatment solution of peach flower extract were prepared by diluting peach flower extract of example 1 at 0.2% vol/vol, 0.5% vol/vol or 1% vol/vol.

Alamar Blue Protocol—Assay for Cell Proliferation Determination

Materials 96 well plate
Alamar Blue Solution Invitrogen, Cat # DAL1100
Dulbecco's Modified Eagle Media (DMEM) by Life Technologies, Cat #11965092
  Supplemented with:
    Hyclone Fetal Bovine Serum (FBS)@10%, Cat # SH30071.03

Methods 96 well plate was seeded with 20,000 cells per well of 62-year-old passage 11 Normal Dermal Human Fibroblasts (NHDF's) from Zen Bio Lot # DFM110210B with treatment as per plate layout provided, and allowed to culture under normal cell culture conditions for 48 hours.

At the end of 48 hours, media and treatment were removed and a 10% solution of Alamar Blue in media was created, and 100 ul of this solution was pipetted into all wells of the plate.

The plate was then returned to the incubator, under standard cell culture conditions for 1 hour. At the end of the hour incubation, the absorbance at 570 nm was measured on a plate reader.

Results were analyzed by graphing the O.D. at 570 nm vs. samples tested.

Results:

Alamar blue reading is proportional to the number of cells that are alive in the plate. By treating with the peach flower extract, which supports Sirt2, we measured an increase of cell number in mature human dermal fibroblasts (62 yr-old).

Conclusion:

The support of SIRT2 in mature skin cells is helping them to proliferate, which makes sense as SIRT2 is related to the cytoskeleton on the microtubules, which are essential for cells to divide.

Figure 8:
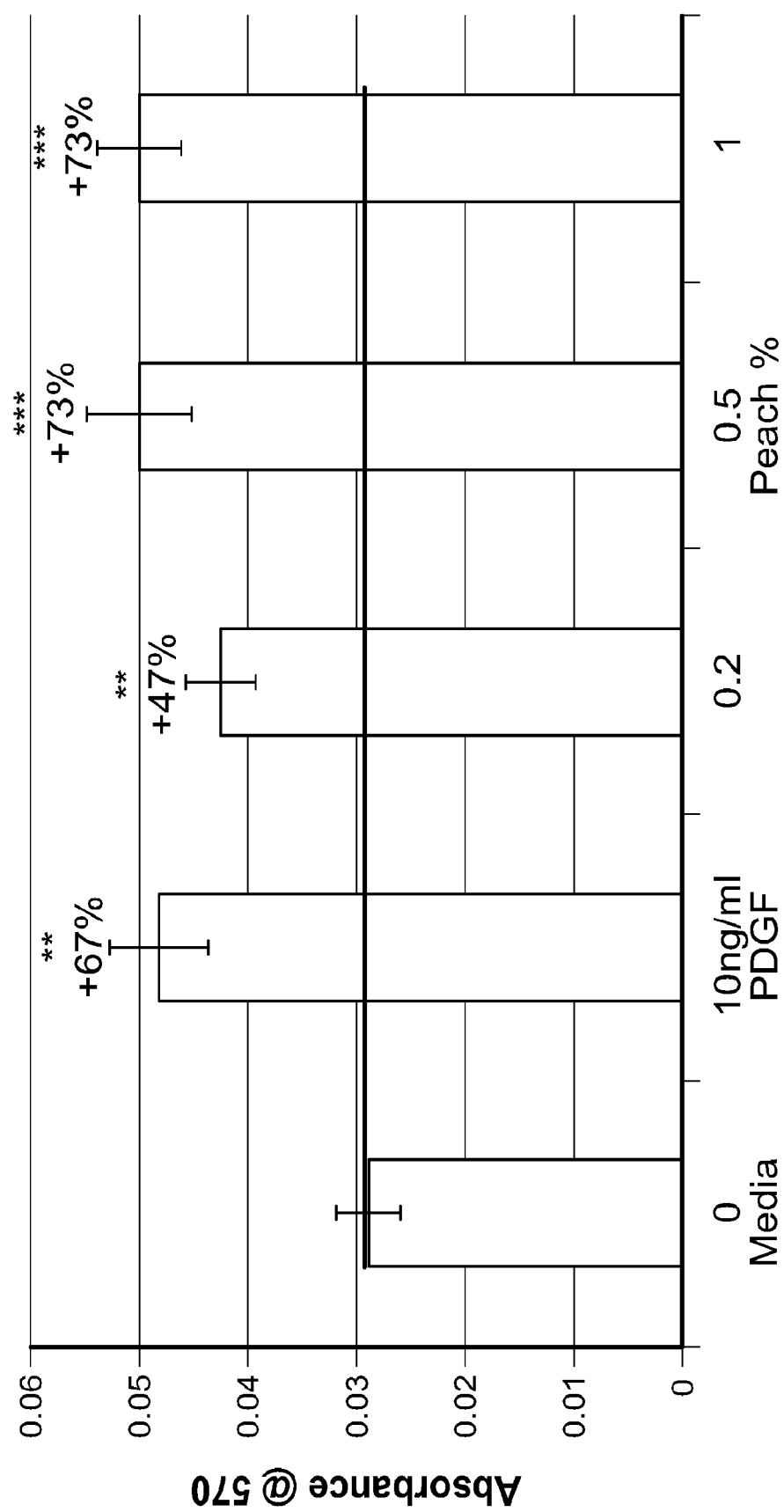
FIG. 8 is illustration of the average cell number measured through absorbance @ 570 nm

The results are illustrated in FIG. 8.

TABLE 9

Average cell number measured through absorbance @ 570 nm after treatment with peach flower extract

| | Peach flower extract (0.2%) | Peach flower extract (0.5%) | Peach flower extract (1%) |
|---|---|---|---|
| Absorbance @ 570 nm | +47%** | +73%*** | +73%*** |

The invention claimed is:

1. A process for obtaining an extract from *Prunus persica* L. comprising:
   (i) adding water to *Prunus persica* L. to make a mixture;
   (ii) agitating said mixture for 2 hours and maintaining the temperature of the mixture from 25° C. to 70° C.;
   (iii) filtering the mixture to remove solid *Prunus persica* L. am thus obtain the extract;
   (iv) pasteurizing the extract overnight at a temperature below 70° C., wherein said extract of step (iv) is further clarified by sequential filtration from about 50 pm to about 20 pm porosity until about 0.5 pm to about 0.2 pm to yield the extract from *Prunus persica*, and wherein said *Prunus persica* extract of step (iv) is then diluted in a solvent selected from the group consisting of water, glycerol, ethanol, propanediol, butylene glycol, dipropylene glycol, ethoxylated or propoxylated glycols, cyclic polyols and mixtures thereof.

* * * * *